United States Patent [19]

Aburaki et al.

[11] Patent Number: 5,837,828
[45] Date of Patent: *Nov. 17, 1998

[54] PRADIMICIN DERIVATIVES

[75] Inventors: Shimpei Aburaki, Kawasaki; Tetsuro Yamasaki; Toshikazu Oki, both of Yokohama; Seiji Iimura, Tokyo; Hajime Kamachi, Urayasu; Hideo Kamei, Tokyo; Takayuki Naito, Kawasaki, all of Japan

[73] Assignee: Bristol-Myers Squibb Co., Princeton, N.J.

[*] Notice: The term of this patent shall not extend beyond the expiration date of Pat. No. 5,410,029.

[21] Appl. No.: 378,201

[22] Filed: May 2, 1995

Related U.S. Application Data

[62] Division of Ser. No. 866,131, Apr. 8, 1992, abandoned.

[51] Int. Cl.$^6$ .............................. C07H 1/00; C07H 15/24
[52] U.S. Cl. ...................... 536/6.4; 536/18.1; 536/18.5
[58] Field of Search ................... 536/6.4, 18.1, 536/18.5

[56] References Cited

U.S. PATENT DOCUMENTS

| 4,870,165 | 9/1989 | Oki et al. | 536/6.4 |
| 4,973,673 | 11/1990 | Sawada et al. | 536/6.4 |
| 4,992,425 | 2/1991 | Nishio et al. | 514/33 |
| 5,227,370 | 7/1993 | Kamachi et al. | 514/27 |
| 5,410,029 | 4/1995 | Aburaki et al. | 536/6.4 |
| 5,608,044 | 3/1997 | Okuyama et al. | 536/6.4 |

FOREIGN PATENT DOCUMENTS

| 315147 | 5/1989 | European Pat. Off. |
| 420552 | 4/1991 | European Pat. Off. |
| 3-294289 | 12/1991 | Japan |

OTHER PUBLICATIONS

ICAAC Abstract No. 984, Oct. 4–7, 1987, New York, New York.

Tomio Takeuchi, et al., "New Antifungal Antibiotics, Benanomicins A and B from an Actinomycete", *J. Antibiot.*, 1988, 41 (6):807–811.

Shuichi Gomi, et al., The Structures of New Antifungal Antibiotics, Benanomicins A and B, *J. Antibiot.*, 1988, 41 (8):1019–1028.

*Primary Examiner*—Elli Peselev
*Attorney, Agent, or Firm*—Prabodh I. Almaula

[57] ABSTRACT

The present invention concerns neutral sugar derivatives of pradimicins, their use as antifungal agents, methods for their preparation, and intermediates for their synthesis.

3 Claims, No Drawings

PRADIMICIN DERIVATIVES

This application is a divisional of application Ser. No. 07/866,131, filed Apr. 8, 1992, now abandoned.

BACKGROUND OF THE INVENTION

1. Field of the Invention

The present invention relates to semi-synthetic antifungal compounds, their therapeutic use, pharmaceutical compositions containing them, and methods for their preparation. More particularly, these antifungal compounds are derivatives of pradimicins.

2. Background Art

Pradimicins, also known as BU-3608 antibiotics, are a group of antifungal antibiotics produced by *Actinomadura hibisca* sp. nov. Various pradimicins that have been isolated from fermentation broths of *Actinomadura hibisca* or variants or mutants thereof, and their structures are depicted below:

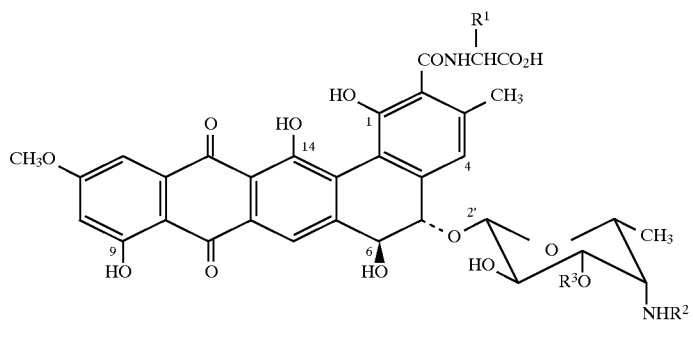

Pradimicin

A: $R^1=CH_3$; $R^2=CH_3$; $R^3=\beta$- D-xylosyl
B: $R^1=CH_3$; $R^2=CH_3$; $R^3=H$
C: $R^1=CH_3$; $R^2=H$; $R^3=\beta$- D-xylosyl
D: $R^1=H$; $R^2=CH_3$; $R^3=\beta$-D-xylosyl
E: $R^1=H$; $R^2=H$; $R^3=\beta$-D-xylosyl FA-1: $R^1=Ch_2OH$; $R^2=CH_3$; $R^3=\beta$-D-xylosyl
FA-2: $R^1=CH_2OH$; $R^2=H$; $R^3=\beta$-D-xylosyl Pradimicin A was reported as BMY-28567 in Abstract No. 984 of the 27th Interscience Conference on Antimicrobial Agents and Chemotherapy, Oct. 4–7, 1987, New York, N.Y.

Pradimicins A, B, C, and the aglycone are disclosed in European Patent Application No. 277,621.

Pradimicins D and E, and their respective desxylosyl analogs are disclosed in our co-pending application, U.S. Ser. No. 203,776, filed Jun. 7, 1988.

Pradimicins FA-1 and FA-2, their respective desxylosyl derivatives, N-alkyl derivatives thereof, and the aglycone are disclosed in our co-pending application, U.S. Ser. No. 269,821, filed Nov. 10, 1988.

Two compounds, known as benanomicins A and B, were reported in *J. Antibiot.*, 1988, 41 (6):807–811, and *ibid*, 41 (8):1019–1028. Benanomicin B appears to be identical to pradimicin C, whereas benanomicin A has the following structure II:

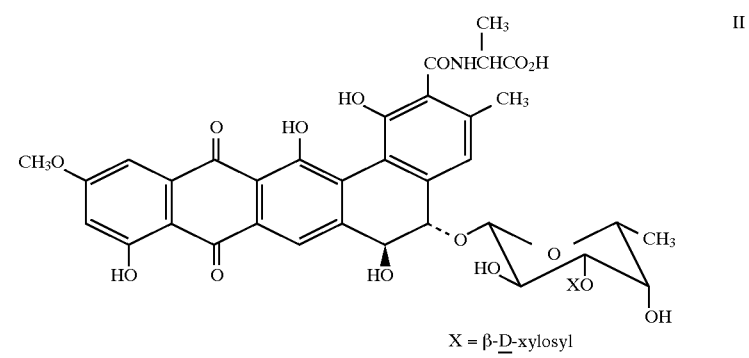

$X = \beta\text{-}\underline{D}\text{-xylosyl}$

Desxylosyl benanomicin B was also disclosed but desxylosyl benanomicin A was not.

SUMMARY OF THE INVENTION

The present invention provides compounds of formula III

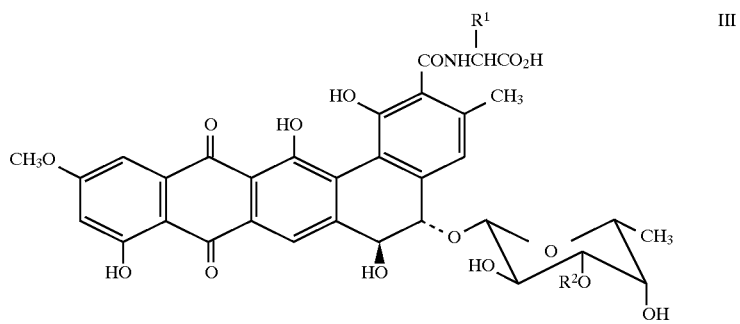

wherein $R^1$ is selected from the group consisting of hydrogen, methyl, and hydroxymethyl, and when $R^1$ is methyl or hydroxymethyl, the resulting amino acid residue has the D-configuration; and $R^2$ is selected from hydrogen or β-D-xylosyl with the proviso that when $R^1$ is methyl $R^2$ is hydrogen; or a pharmaceutically acceptable salt thereof.

Another aspect of the present invention provides intermediates of formula IV

D-configuration; $R^c$ is $C_{1-5}$ alkyl; and $R^d$ is $C_{1-5}$ alkanoyl. Compounds of formula IV are useful intermediates in the preparation of compound of formula III as well as other pradimicin derivatives. Also provided is a method for the preparation of IV which comprises reacting a pradimicin aglycone ester with an acyl halide in the presence of a phase transfer catalyst.

A further aspect of the present invention provides compounds of formulas V and VI

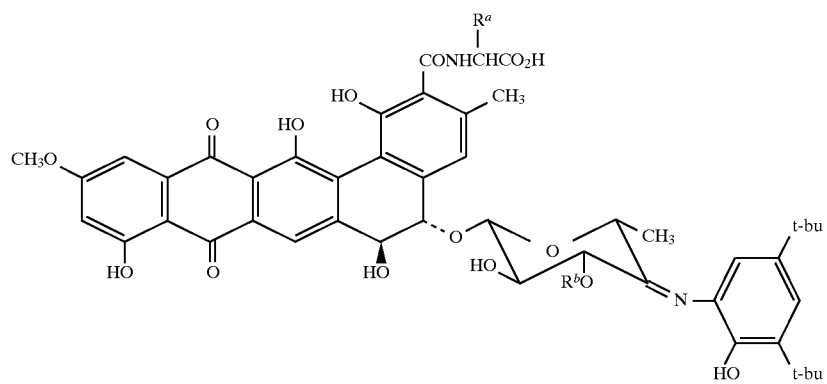

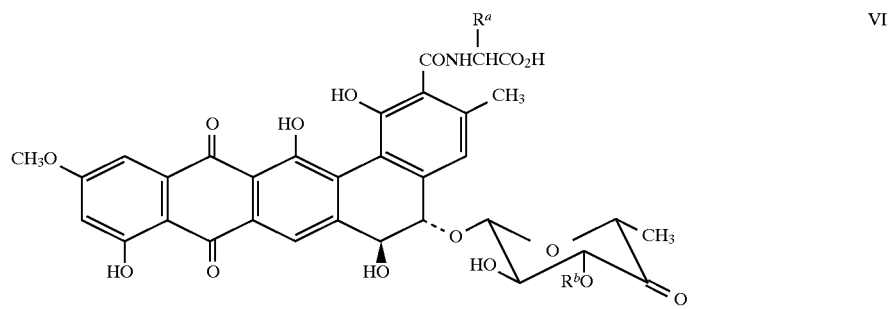

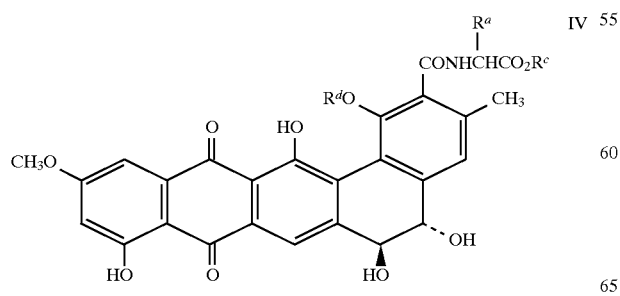

wherein $R^a$ is H, methyl, or hydroxymethyl, and when $R^a$ is methyl or bydroxymethyl the resulting amino acid has the D-configuration; $R^b$ is H or β-D-xylosyl; or a salt thereof, or an ester thereof. Compounds of formulas V and VI are useful intermediates for the preparation of compounds of formula III.

Yet a further aspect of the present invention provides a process for preparing a compound of formula VII

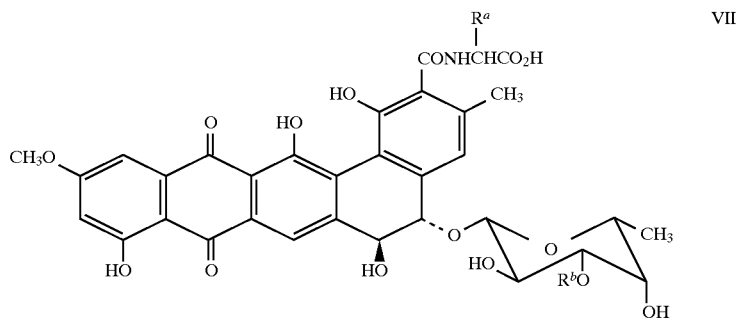

VII wherein $R^a$ and $R^b$ are as previously defined, or a pharmaceutically acceptable salt thereof, which comprises the steps of (a) reacting a pradimicin having a primary amino group with 3,5-di-t-butyl-1,2-benzoquinone in an inert organic solvent to provide the corresponding imine; (b) converting the imine into the corresponding ketone in the presence of an acid catalyst; (c) reducing the ketone to the hydroxyl group; and (d) separating the isomers.

DETAILED DESCRIPTION OF THE INVENTION

As used herein, unless indicated otherwise explicitly or by context, the term "pharmaceutically acceptable salt" refers to salts formed with inorganic or organic bases and includes, but is not limited to, sodium, potassium, lithium, calcium, magnesium, ammonium, and trialkylammonium salts; "pradimicin" represents a member of the naturally occurring pradimicins, their desxylosyl derivatives, and salts thereof. "Pradimicin aglycone" refers to a compound having the formula VIII

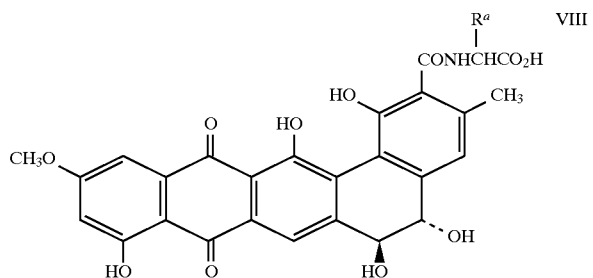

VIII wherein $R^a$ is as defined under formula IV.

The pradimicin starting materials and methods for their production are disclosed in our co-pending applications, U.S. Ser. No. 115,273, filed Nov. 2, 1987, U.S. Ser. No. 203,776, filed Jun. 7, 1988, U.S. Ser. No. 221,144, filed Jul. 19, 1988, and U.S. Ser. No. 269,821, filed Nov. 10, 1988. The disclosures contained in these applications are hereby incorporated by reference. The pradimicins may be used as the free base, acid or base addition salts, the internal salt, or esters of the carboxylic group, depending on the particular reaction conditions. Base salts may be, e.g., sodium, potassium, lithium, calcium, magnesium, ammonium, and trialkylammonium salts; acid addition salts may be, e.g., hydrochloride, sulfate, nitrate, and the like; carboxylic acid ester may be a lower alkyl ester, e.g. methyl, ethyl, and isopropyl or a cycloalkyl ester, e.g., cyclohexyl, phenyl, or benzyl ester.

Compounds of formula III may be prepared by two general methods: (1) glycosidation of an 1-O-acylated pradimicin aglycone ester with the appropriate monosaccharide or disaccharide; or (2) conversion of the sugar amino group of a pradimicin into a keto group followed by reduction to a hydroxyl group. These two approaches are illustrated schematically and discussed in detail below.

Scheme I. Glycosidation of Pradimicin Aglycone

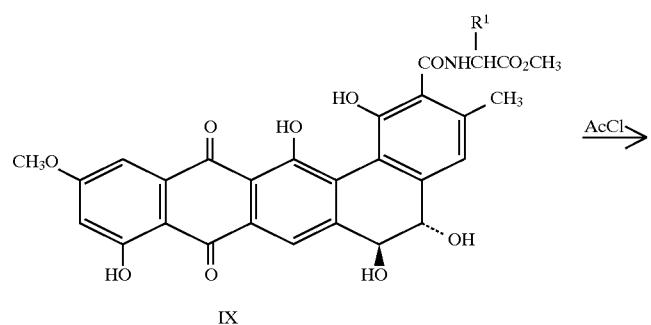

IX

-continued
Scheme I. Glycosidation of Pradimicin Aglycone

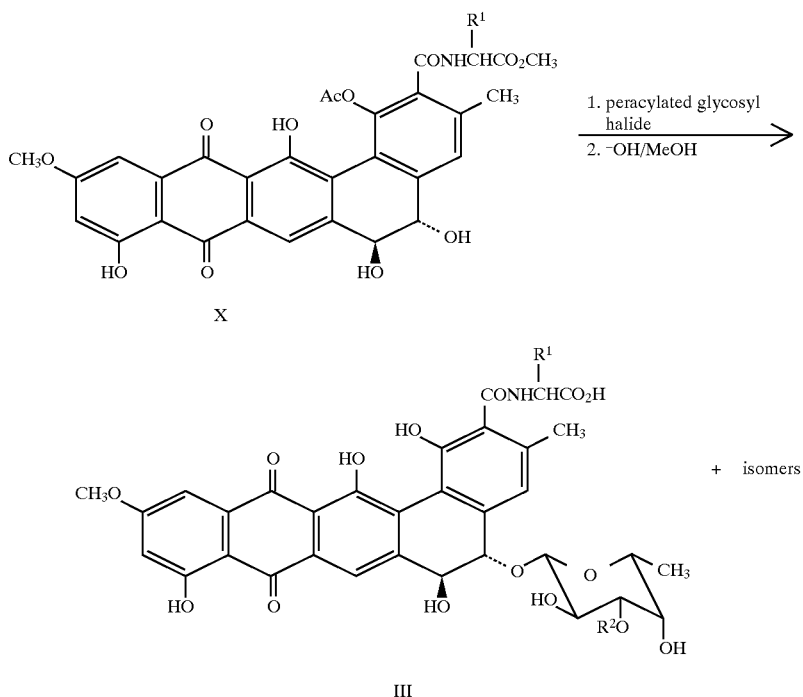

In Scheme I, $R^1$ and $R^2$ are as previously defined under formula III. Pradimicin aglycone esters of formula IX are generally insoluble or poorly soluble in organic solvents such as methylene chloride, chloroform, dichloroethane, and dioxane making it inconvenient as starting material for direct glycosidation with the desired sugar. Thus one aspect of the present invention is the conversion of IX into a corresponding solvent soluble acylated derivative. The pradimicin aglycone ester IX is acylated under phase transfer conditions using as acylating agent such as an acyl halide. Suitable acyl halides are for example acetyl chloride and propionyl chloride. The reaction is conducted in an inert organic solvent such as methylene chloride, tetrahydrofuran, ether, and dioxane and toluene. The reaction mixture includes a base in solid form; suitable bases include sodium hydroxide, potassium hydroxide, sodium bicarbonate, sodium carbonate and the like. The phase transfer catalyst may be for example tetrabutylammonium hydrogen sulfate, tetrabutylammonium dihydrogen phosphate, as well as other reagents that can bring the pradimicin reactant into the same phase as the acylating reagent. The reaction may be carried out at temperatures ranging from about −50° C. to about 50° C., but preferably it is carried out at room temperature. The reaction time may range from several minutes to several hours. In a preferred embodiment the acylation is effected in an organic solvent using acetyl chloride in the presence of tetrabutylammonium hydrogen sulfate (TBAH) and powdered sodium hydroxide; the reaction using these reagents generally takes less than one hour to complete at room temperature. Phase transfer catalyzed acylation using TBAH/NaOH/organic solvent is described by Illi, V.O. in Tet. Lett., 1979, 2431–2432. Using the procedure provided herein above, the phenolic hydroxyl group at the 1-position is preferentially acylated over the aliphatic hydroxyl groups and the phenolic hydroxyl groups at the 9- and 14-positions.

The acylated pradimicin aglycone ester X is then glycosylated under Koenigs-Knorr conditions. Typically, a peracylated glycosyl halide such as peracetylated fucosyl bromide or peracetylated 3-O-(β-D-xylopyranosyl) fucosyl bromide is used, and the reaction is carried out in an inert organic solvent such as methylene chloride, chloroform, 1,2-dichloroethane, dioxane, and the like, under anhydrous conditions and in the presence of a silver or mercuric salt such as mercuric cyanide and mercuric bromide. Anhydrous conditions may be maintained by including in the reaction mixture a dehydrating agent such as molecular sieves. Glycosylation is preferably performed at an elevated temperature for a period sufficient to substantially convert the aglycone into the glycoside. The reaction between 1-O-acetylated pradimicin A aglycone methyl ester and fucosyl bromide at about 80° C. is usually complete in two hours or less. The various ester linkages are then hydrolyzed using conventional methods to remove the phenolic and sugar acyl groups, as well as the amino acid ester group. A suitable method is, e.g., base-catalyzed saponification at room temperature. The glycosidation generally results in a mixture of regioisomers and anomers, including 5-O-α-, 5-O-β-, and 6-O-β-glycosylated products. The individual components may be separated using techniques well known in the art, such as column chromatography, and may be done before or after the removal of the protecting groups.

It will be appreciated that 1-O-acylated pradimicin aglycone esters may be used to prepare pradimicin compounds other than the ones illustrated in Scheme I if the appropriate sugar is used.

Scheme II. Reduction of Ketone

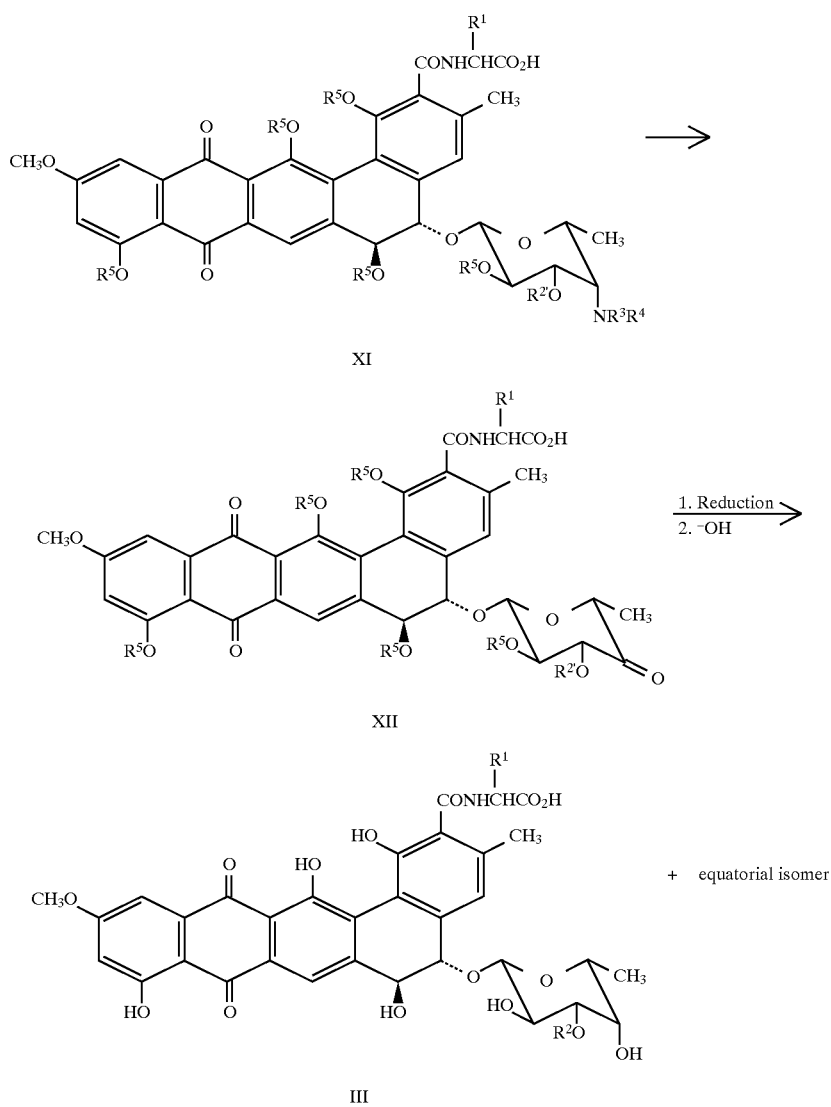

In the above Scheme, $R^1$ and $R^2$ are as defined previously under formula III; $R^{2'}$ is H, β-D-xylosyl; $C_{1-5}$ alkanoyl, preferably acetyl; or peracylated, preferably peracetylated β-D-xylosyl; $R^3$ and $R^4$ are independently H or methyl; and $R^5$ is H or acetyl A variety of methods have been reported in the art for converting an amine into a carbonyl compound. For example, primary amines can be so transformed by treatment with a reagent, such as benzothiazole-2-carboxaldehyde or 3,5-di-t-butyl-1,2-benzoquinone, to give the imine which is then hydrolyzed to the corresponding carbonyl compound. Primary, secondary, and tertiary amines can be directly oxidized to the corresponding carbonyl compounds with, e.g., manganese oxide or neutral permanganate. Tertiary amines may be oxidized with, e.g., m-chloroperbenzoic acid to its amine oxide which, in turn, is converted to the carbonyl compound by treatment with, e.g., trifluoroacetic anhydride. Under certain reaction conditions, e.g. oxidizing conditions, it may be desirable to protect non-reacting functional groups on the pradimicin starting material, such as the alcoholic and phenolic OH groups; the protection and deprotection of these functional groups are well within the skills of a person of ordinary skill in the art. Reduction of the carbonyl may be effected using a reducing agent such as sodium borohydride. The reduction is not stereospecific and results in a mixture of products where the carbonyl derived hydroxyl group is in either the axial or the equatorial position. The mixture may be separated by chromatography. In our experience, compounds of the present invention may be prepared via the imine generated by treatment of a pradimicin having a primary amine group with 3,5-di-t-butyl-1,2-benzoquinone. This procedure is illustrated in Scheme III and will be further elaborated below with the understanding that the preparation of compounds of the invention is not limited to the method particularly exemplified.

Scheme III. Preparation of (III) via Imine

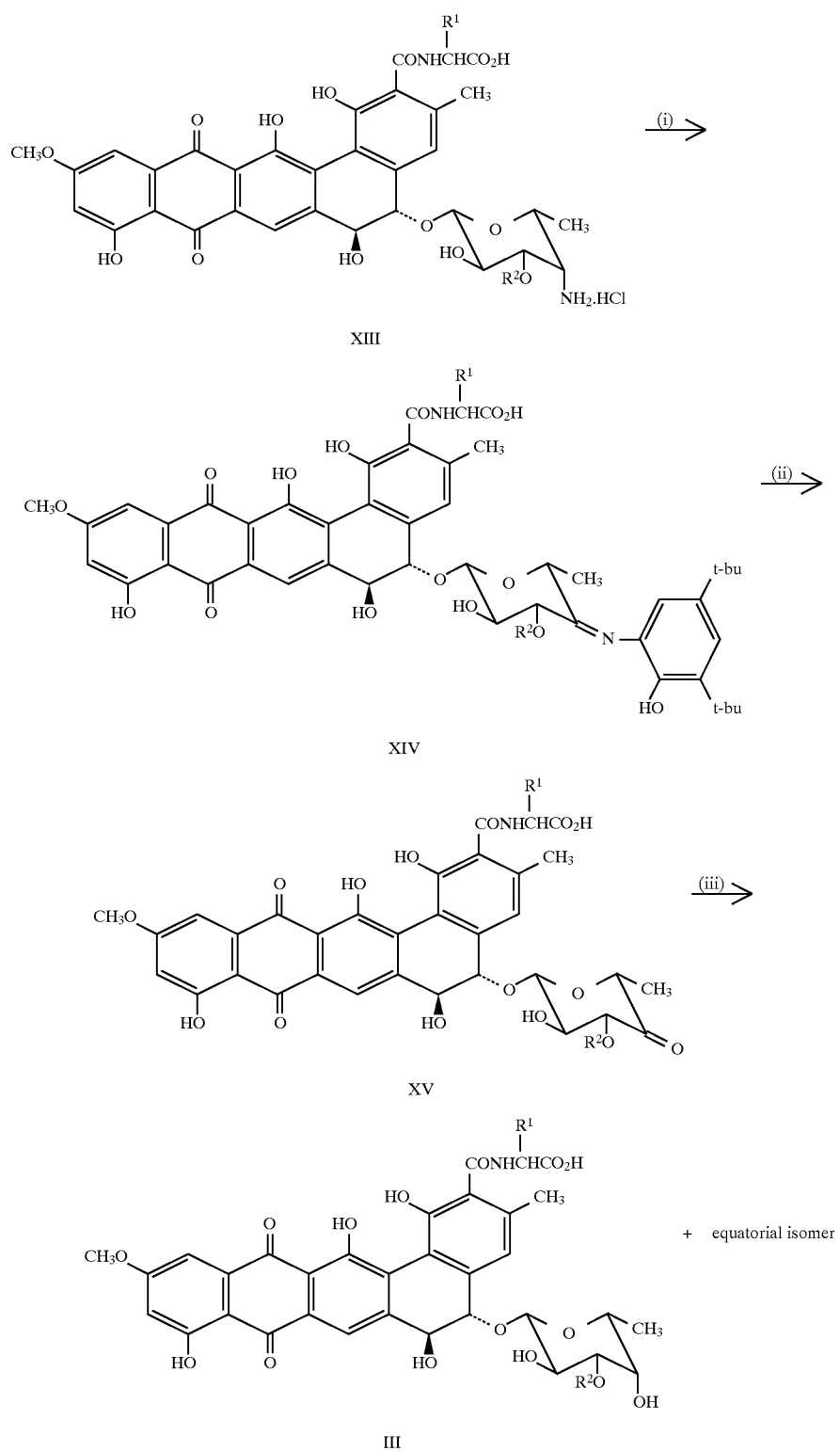

(i) 3,5-di-t-butyl-1,2-benzoquinone, NEt₃ in MeOH; (ii) HCO₂H/MeOH; (iii) NaBH₄.

In the above Scheme, $R^1$ and $R^2$ are as defined previously under Formula III. To elaborate on the above scheme, pradimicin is first reacted with 3,5-di-tert-butyl-1,2-benzoquinone to convert the primary amino group on the sugar moiety to the corresponding 2-hydroxy-3,5-di-tert-butylphenyl Schiff base (XIV). The reaction is carried out in solution using a reaction inert solvent, such as a lower alkanol, preferably methanol. A tertiary amine base, such as triethylamine, is preferably included in the reaction mixture when an acid addition salt of pradimicin is used as the starting material. The temperature of the reaction is not critical and the reaction may be conveniently conducted at ambient temperature. In general, the reaction takes from about 20 minutes to several hours. The imine thus obtained is hydrolyzed in the presence of an acid to yield the ketone (XV). The acid is not particularly restricted and may be an inorganic acid or an organic acid, such as formic, acetic, oxalic acid, and the like. The hydrolysis may be carried out in a lower alkanol, such as methanol, at a temperature ranging from room temperature to the refluxing temperature of the reaction solution. The ketone is then reduced to the alcohol by a conventional reducing agent; a suitable agent is, for example, sodium borohydride. The reduction using sodium borohydride is preferably carried out at a reduced temperature, for example, from about $-10°$ C. to about $10°$ C. in an aqueous or alcoholic solution. The product of the reduction is a mixture of axial and equatorial hydroxy compounds which are separable by chromatography for example on a $C_{18}$ column.

It will be noted that the methods described herein for synthesizing the novel compounds of the present invention are also applicable for preparing the known compound benanomicin A when the appropriate starting materials are used.

BIOLOGICAL PROPERTIES

The minimum inhibitory concentrations (MICs) of representative compounds of the present invention against 14 fungi were determined by serial agar dilution method using Sabouraud dextrose agar (pH 7.0). The inoculum size of the test organism was adjusted to $10^6$ cells/ml, and approximately 0.003 ml of fungal suspension was applied to the surface of agar plates containing the test antibiotics. After the plates had been incubated for 40 hours at $28°$ C., the lowest concentration of antibiotic causing virtually complete inhibition of fungal growth was determined as the MIC. The results are summarized in Table I.

TABLE I

In Vitro Antifungal Actvity

| Test Organisms | | Ex. 1 | Ex. 2 | Ex. 3 |
|---|---|---|---|---|
| Candida albicans | IAM4888 | 25.0 | 12.5 | 12.5 |
| Candida albicans | A9540 | 25.0 | 12.5 | 12.5 |
| Cryptococcus neoformans | D49 | 50.0 | 12.5 | 12.5 |
| Cryptococcus neoformans | IAM4514 | 50.0 | 12.5 | 6.3 |
| Aspergillus fumigatus | IAM2530 | >50.0 | 25.0 | 25.0 |
| Aspergillus fumigatus | IAM2034 | >50.0 | 50.0 | 25.0 |
| Fusarium moniliforme | A2284 | >50.0 | >50.0 | >50.0 |
| Trichophyton mentagrophytes | D155 | >50.0 | 12.5 | 50.0 |
| Trichophyton mentagrophytes | #4329 | >50.0 | 12.5 | 50.0 |
| Sporothrix schenckii | IFO8158 | >50.0 | 25.0 | 12.5 |
| Aspergillus flavus | FA21436 | >50.0 | >50.0 | >50.0 |
| Blastomyces dermatitidis | D40 | >50.0 | >50.0 | 50.0 |
| Petriellidium boydii | IFO8078 | ND | >50.0 | >50.0 |
| Mucor spinosus | IFO5317 | >50.0 | >50.0 | 50.0 |

The in vivo activity of compound of Example 1 was tested against *Candida albicans* A9540 infection in mice. Test organisms were cultured for 18 hours at $28°$ C. in YGP medium (yeast extract, glucose, peptone, $K_2HPO_4$, $MgSO_4$) and then suspended in saline. Male ICR mice weighing 20 to 24 g were infected intravenously with about 10 times the median lethal dose of the test fungus. The antibiotic at various dose levels was administered to groups of 5 mice each intravenously just after the fungal infection. The dose that protects 50% of the animals from infection ($PD_{50}$, mg/kg) was calculated from survival rates recorded on the 20th day after the fungal challenge. All control animals died within 7 to 15 days after infection. Compound of Example 1 showed no significant in vivo activity at 50 mg/kg by a single intravenous injection.

For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration. Preparations for parenteral administration include sterile aqueous or non-aqueous solutions, suspensions, or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that, when treating a host infected with a fungus susceptible to the antibiotics of this invention, the actual preferred route of administration and dosage used will be at the discretion of the attending clinician skilled in the treatment of fungal infections and will vary according to the causative organism, its sensitivity to the antibiotic, severity and site of the infection, and patient characteristics, such as age, body weight, rate of excretion, concurrent medications, and general physical condition.

The following examples are illustrative without limiting the scope of the present invention. The structures of all the compounds prepared in the following examples are given at the end of the Examples section.

Example 1. Preparation of 4'-deamino-4'-hydroxy pradimicin B (XIX)

(a) To a suspension of pradimicin A aglycone methyl ester (IX, $R^1=CH_3$; 154 mg, 0.27 mmol) in dry dioxane (3 ml) were sequentially added tetrabutylammonium hydrogen sulfate (103 mg, 0.30 mmol), powdered NaOH (85 mg, 2.12 mmol), and 1M solution of acetyl chloride in dry dioxane (1.06 ml). The mixture was stirred at room temperature for 30 minutes under argon atmosphere, and the insoluble matters were removed by filtration and washed with dioxane. The filtrate and washings were combined and evaporated to dryness, and the residue was chromatographed on silica gel (40 g) using chloroform/methanol=20/1 as eluant to afford 1-O-acetylated pradimicin A aglycone methyl ester (XVI, 69 mg, 42%) as orange solid. MP $220°$ C. (dec.).

IR $v_{max}$ (KBr) cm$^{-1}$ 1749, 1612.

UV $\lambda_{max}$ (CH$_3$CN) nm ($\epsilon$) 288 (25600), 448 (10300).

$^1$H NMR (DMSO-d$_6$) $\delta$ 1.33 (3H, d, J=7.3 Hz, 17-CH$_3$), 2.02 (3H, s, OAc), 2.37 (3H, s, 3-CH$_3$), 3.67 (3H, s, COOCH$_3$), 3.95 (3H, s, 11-OCH$_3$), 4.22 and 4.29 (each 1H, m, $J_{5,6}$=11.1 Hz, 5 and 6-H), 4.41 1H, dq, $J_{17,NH}$=6.9 Hz, 17-H), 6.13 and 6.30 (each 1H, brs, 5 and 6-OH), 6.93 (1H, d, $J_{10,12}$=2.4 Hz, 10-H), 7.30 (1H) d, 12-H), 7.46 (1H, s, 4-H), 8.07 (1H, s, 7-H), 8.77 (1H, d, NH), 12.83 (1H, s, 9-OH) and 13.37 (1H, s, 14-OH).

(b) To a solution of 1-O-acetylated pradimicin A aglycone methyl ester (73 mg, 0.12 mmol) in absolute chloroform (4 ml) were added powdered molecular sieves 3A (740 mg), Hg(CN)$_2$ (271 mg, 1.07 mmol), and HgBr$_2$ (121 mg, 0.34 mmol). The mixture was stirred at room temperature for 2 hours, and tri-O-acetyl-D-fucosyl bromide [prepared from tetra-O-acetyl-D-fucose (133 mg, 0.40 mmol) and 30% HBr–AcOH (1.3 ml) according to the reported procedure by M. Takai, et al., J. Med. Chem 23, 549 (1980)] was added. The mixture was heated at 80° C. for 1.5 hours and then filtered off and washed with chloroform. The filtrate and washings were combined, washed with water then saturated aqueous NaCl, and dried over $Na_2SO_4$. The solvent was evaporated, and the residual syrup was chromatographed on silica gel (20 g) using toluene/ethyl acetate=1/1, and chloroform/methanol=20/1, successively, as eluants to afford the glycosidated product as a mixture of several components (43 mg, Y:41%).

IR $v_{max}$ (KBr) $cm^{-1}$ 1751, 1623.

UV $\lambda_{max}$ ($CH_3CN$) nm ($E_{1\ cm}^{1\%}$) 278 (177), 494 (71).

(c) A crude sample obtained above (38 mg) was treated with 1N NaOH (1.2 ml) in methanol (6 ml) at room temperature for 2 hours. The mixture was adjusted to pH 4 with 1N HCl and then evaporated to dryness. The residue was chromatographed on a $C_{18}$ column using acetonitrile/phosphate buffer (pH 3.5)=35/65 as eluant to afford 3 fractions. Each fraction was made alkaline with 1N NaOH and then placed on a $C_{18}$ column, washed with $H_2O$, eluted with 50% aqueous acetonitrile, and lyophilized to afford the following fractions as sodium salt.

Fraction 1: 4'-Deamino-4'-hydroxy pradimicin B α-anomer (XVII, 6 mg, 19%). MP>230° C.

IR $v_{max}$ (KBr) $cm^{-1}$ 1618.

UV $\lambda_{max}$ (1/100N NaOH) nm (ε) 319 (7000), 499 (6800).

$^1$H NMR (DMSO-$d_6$) δ 1.08 (3H, d, $J_{5',Me}$=6.4 Hz, 5'-Me), 1.33 (3H, d, $J_{17,Me}$=7.3 Hz, 17-Me), 2.26 (3H, s, 3-Me), ca. 3.50 (2H, m, 3',4'-H), ca. 3.65 (1H, m, 2'-H), 3.91 (3H, s, 11-OMe), 4.12 (1H, q, 5'-H), 4.30 (1H, d, $J_{5,6}$=9.0 Hz, 5-H), ca. 4.30 (1H, m (q after addition of $D_2O$ ), 17-H), 4.43 (1H, dd, $J_{6,OH}$=3.9 Hz, 6-H), ca. 4.5 (1H, m, OH), ca. 4.6 (2H, m, OH×2), 4.81 (1H, d, $J_{1',2'}$=2.6 Hz, 1'-H), 5.62 (1H, d, 6-OH), 6.71 (1H, d, $J_{10,12}$=2.6 Hz, 10-H), ca. 7.05 (1H, brs, 4-H), 7.12 (1H, d, 12-H), and 7.63 (1H, s, 7-H).

Fraction 2: 6-P-(β-D-fucopyranosyl) pradimicin A aglycone (XVIII, 10 mg, 32%). MP>230° C.

IR $v_{max}$ (KBr) $cm^{-1}$ 1617.

UV $\lambda_{max}$ (1/100N NaOH) nm (ε) 316 (11200), 498 (10300).

$^1$H NMR (DMSO-$d_6$+$D_2O$) δ 1.14 (3H, d, $J_{5',\ Me}$=6.0Hz, 5'-Me), 1.29 (3H, d, $J_{17,Me}$=6.8 Hz, 17-Me), 2.23 (3H, s, 3-Me), 3.43 (1H, d, $J_{3',4'}$=3.9 Hz, 4'-H), 3.48 (1H, dd, $J_{2',3'}$=9.0 Hz, 3'-H), 3.52 (1H, d, $J_{1',2'}$=7.3 Hz, 2'-H), 3.56 (1H, q, 5'-H), 3.86 (1H, q, 17-H), 3.89 (3H, s, 11-OMe), 4.38 (1H, d, $J_{5,6}$=11.1 Hz, 6-H), 4.42 (1H, d, 5-H; simplified after addition of $D_2O$), 4.58 (1H, d, 1'-H), 6.70 (1H, br d, 10-H), 6.83 (1H, s, 4-H), 7.13 (1H, br d, 12-H), and 7.78 (1H, s, 7-H).

Fraction 3: 4'-Deamino-4'-hydroxy pradimicin B (XIX, 2 mg, 6%). MP>230° C.

IR $v_{max}$ (KBr) $cm^{-1}$ 3396, 1620.

UV $\lambda_{max}$ (1/100N-NaOH) nm (ε) 319 (10700), 498 (10400).

$^1$H NMR (DMSO-$d_6$+$D_2O$) δ 1.14 (3H, d, $J_{5',Me}$=6.4 Hz, 5'-Me), 1.31 (3H, d, $J_{17,Me}$=6.8 Hz, 17-Me), 2.23 (3H, s, 3-Me), 3.39 (1H, dd, 3'-H), 3.44 (1H, d, $J_{3',4'}$=3.4 Hz, 4'-H), 3.53 (1H, dd, $J_{1',2'}$=8.1 Hz, $J_{2',3'}$=9.0 Hz, 2'-H), 3.57 (1H, q, 5'-H), 3.85 (1H, q, 17-H), 3.91 (3H, s, 11-OMe), 4.37 (1H, d, $J_{5,6}$=11.1 Hz, 5-H), 4.46 (1H, d, 6-H; simplified after addition of $D_2O$), 4.53 (1H, d, 1'-H), 6.66 (1H, br d, 10-H), 6.99 (1H, s, 4-H), 7.15 (1H, br d, 12-H), and 7.68 (1H, s, 7-H).

Mass (HR-FAB) m/z 695.1832; Calcd. for $C_{34}H_{33}NO_{15}$: 695.1813

Example 2. Preparation of 4'-deamino-4'-hydroxy pradimicin E (XXII)

(a) Triethylamine (0.15 ml, 1.05 mol) was added to a mixture of pradimicin E HCl (150 mg, 0.18 mmol), and 3,5-di-tert-butyl-1,2-benzoquinone (110 mg, 0.5 mmol) in dry methanol (4.5 ml). The mixture was stirred overnight and concentrated under reduced pressure. To the residue were added ethyl acetate (5 ml) and aq. saturated $NaHCO_3$ (2 ml), and the mixture was stirred for 30 minutes at room temperature to precipitate the sodium salt of 4'-(3,5-di-t-butyl-2-hydroxy)phenyl imine of pradimicin E (XX, 205 mg).

IR $v_{max}$ (KBr) $cm^{-1}$ 1617, 1258, 1078.

UV $\lambda_{max}$ (methanol) nm ($E_{1\ cm}^{1\%}$): 284 (225), 495 (91).

$^1$H NMR (DMSO-$d_6$) δ:0.95 (3H, d, J=7 Hz, 5'-$CH_3$), 1.21 (9H, s t-Bu), 1.24 (9H, s, t-Bu), 2.23 (3H, s, 3-$CH_3$), 4.81 (1H, d, J=8 Hz, 1'-H), 5.15 (2H, br)*, 5.99 (1H, s)*, 6.43 (1H, d, J=2 Hz, phenyl-H), 6.51 (1H, d, J=2 Hz, phenyl-H), 6.70 (1H, br, 10-H), 6.90 (1H, s, 4-H), 7.10 (1H, br, 12-H), 7.70 (1H, s, 7-H), 15.02 (1H, s)*.

* Disappeared upon addition of $D_2O$.

(b) A mixture of the product obtained in step (a) (200 mg, 0.19 mmol), formic acid (2.5 ml), and methanol (2.5 ml) was heated at 60° C. for 1.5 hours. The reaction mixture was concentrated under reduced pressure, and the residue was chromatographed on a column of C18 silica gel (20×200 mm). The column was eluted with water and then with 80% acetonitrile. The acetonitrile fractions were checked with HPLC, and the desired fractions were combined and concentrated to leave an aqueous residue, which was freeze-dried to give 4'-deamino-4'-oxo pradimicin E (XXI, 84 mg, 89%) as an amorphous powder.

IR $v_{max}$ (KBr) $cm^{-1}$1620, 1260, 1084.

UV $\lambda_{max}$ (0.01N NaOH) nm (ε): 319 (11600), 497 (10700).

$^1$H NMR (DMSO-$d_6$) δ:3.88 (3H, s, $OCH_3$), 6.69 (1H, s, 10-H), 6.90 (1H, s, 4-H), 7.09 (1H, s, 12-H), 7.72 (1H, s, 7-H).

(c) To a stirred mixture of the product obtained in step (b) (90 mg, 0.11 mmol), 1N NaOH (0.25 ml), and water (9 ml) was added an aqueous solution of 0.1M sodium borohydride (0.4 ml) at 5° C. The mixture was stirred for 30 minutes at the same temperature and acidified with 1N $H_2SO_4$ to destroy the reagent. The mixture was adjusted to pH 8 with $NAHCO_3$ and chromatographed on a column of C18 silica gel (40×330 mm, 5% acetonitrile), followed by preparative HPLC (System 500 (Waters), 15% acetonitrile) to give 3 fractions—a faster moving fraction containing the equatorial isomer, a slower moving fraction containing the axial isomer, and a fraction containing a mixture of both isomers. Each fraction was concentrated to a small volume, acidified with 1N $H_2SO_4$, and subjected to a short column of C18 silica gel. The column was washed with water and eluted with 80% acetonitrile. The eluate was concentrated to a small volume and lyophilized. The 3 fractions afforded 4'-deamino-4'-hydroxy pradimicin E axial isomer (XXII, 7.5 mg, 8%), the equatorial isomer (XXIII, 4.8 mg, 5%), and a mixture thereof (8.2 mg, 9%).

4'-Deamino-4'-hydroxy pradimicin E (axial isomer, XXII)

MP:>220° C. (grad. dec.)

UV $\lambda_{max}$ (0.01N NaOH) nm ($E_{1\ cm}^{1\%}$): 236 (317), 319 (151), 496 (140).

IR $v_{max}$ (KBr) $cm^{-1}$3288, 2921, 1728, 1628, 1607.

$^1$H NMR (DMSO-$d_6$) δ:1.1 (3H, d, J=6.4 Hz, 5'-$CH_3$), 2.33 (3H, s, 3-$CH_3$), 3.91 (2H, d, J=6.06 Hz, NH-$CH_2$-), 3.95 (3H, s, 11-$OCH_3$), 4.40 (1H, d, J=7.3 Hz, 1"-H), 4.64 (1H, d, J=7.7 Hz, 1'-H), 6.89 (1H, s, 10-H), 7.11 (1H, s, 4-H), 7.25 (1H, s, 12-H), 7.98 (1H, s, 7-H).

HPLC*: Retention time 9.8 minutes.
The equatorial isomer (XXIII)
MP:>220° C. (grad. dec.)
UV $\lambda_{max}$ (0.01N NaOH) nm ($E_1{}_{cm}^{1\%}$): 241 (271), 320 (128), 498 (121).
IR $\nu_{max}$ (KBr) cm$^{-1}$: 3387, 2920, 1730, 1630, 1605.
$^1$H NMR (DMSO-d$_6$) δ:1.15 (3H, d, J=6.0 Hz, 5'-CH$_3$), 2.31 (3H, s, 3-CH$_3$), 3.90(2H, d, J=5,8 Hz, NH-CH$_2$-), 3.94(3H, s, 11-OCH$_3$), 4.45 (1H, d, J=7.3 Hz, 1"-H), 6.84 (1H, s, 10-H), 7.00 (1H, s, 4-H), 7.21 (1H, s, 12-H), 7.91 (1H, s, 7-H).
HPLC*: Retention time 8.6 minutes.
*HPLC: column, Senshu Pak SSC-ODS-262; solvent, CH$_3$CN:pH 7
buffer=15:85; flow rate, 2 ml/minute.

Example 3. Preparation of 4'-deamino-4'-hydroxy pradimicin FA-2 (XXVI)

(a) Triethylamine (0.20 ml, 1.43 mmol) was added to a mixture of pradimicin FA-2 HCl (150 mg, 0.16 mmol), 3,5-di-tert-butyl-1,2-benzoquinone (150 mg, 0.68 mmol) in dry methanol (2.5 ml). The mixture was stirred overnight and concentrated under reduced pressure. To the residue were added ethyl acetate (5 ml) and aq. saturated NaHCO$_3$ (2 ml), and the mixture was stirred for 30 minutes at room temperature to precipitate the sodium salt of 4'-(3,5-di-t-butyl-2-hydroxy)phenyl imine of pradimicin FA-2 (XXIV, 164 mg, 96%).
IR $\nu_{max}$ (KBr) cm$^{-1}$: 1618, 1259.
UV $\lambda_{max}$ (methanol) nm ($E_1{}_{cm}^{1\%}$): 281 (211), 497 (93).
$^1$H NMR (DMSO-d$_6$) δ:0.95 (3H, d, J=7 Hz, 5'-CH$_3$), 1.22 (9H, s, t-Bu), 1.25 (9H, s, t-Bu), 2.23 (3H, s, 3-CH$_3$), 4.81 (1H, d, J=8 Hz, 1'-H), 5.05 (1H, br)*, 6.42 (1H, d, J=2 Hz, phenyl-H), 6.44 (1H, d, J=2 Hz, phenyl-H), 6.70 (1H, br, 10-H), 6.90 (1H, s, 4-H), 7.10 (1H, br, 12-H), 7.40 (1H, br)*, 7.69 (1H, s, 7-H).
*Disappeared upon addition of D$_2$O.

(b) A mixture of the product obtained in step (a) (160 mg, 0.15 mmol), formic acid (3 ml) and methanol (3 ml) was heated at 60° C. for 1.5 hours. The reaction mixture was concentrated under reduced pressure and the residue was chromatographed on a column of C18 silica gel (20×200 mm). The column was eluted with water and then with 30% acetonitrile. The acetonitrile fractions were checked with HPLC, and the desired fractions were combined and concentrated to leave an aqueous residue which was freeze-dried to give 4'-deamino-4'-oxo pradimicin FA-2 (XXV, 105 mg, 83%) as an amorphous powder.
IR $\nu_{max}$ (KBr) cm$^{-1}$: 1733 (weak), 1607, 1258, 1084.
UV $\lambda_{max}$ (0.01N NaOH) nm (ε): 318 (14800), 498 (13500).
$^1$H NMR (DMSO-d$_6$) δ:3.94 (3H, s, OCH$_3$), 6.88 (1H, s, 10-H), 7.25 (1H, s, 12-H), 7.95 (1H, s, 7-H).

(c) To a stirred mixture of the product obtained in step (b) (121 mg, 0.15 mmol), 1N NaOH (0.3 ml), and water (12 ml) was added an aqueous solution of 0.1M sodium borohydride (0.7 ml) at 5° C. The mixture was stirred for 1 hour at the same temperature and acidified with 1N H$_2$SO$_4$ to destroy the reagent. The mixture was adjusted to pH 8 with NaHCO$_3$ and chromatographed on a column of C18 silica gel (40×330 mm, 5% acetonitrile) and followed by preparative HPLC (System 500 (Waters), 7% acetonitrile) to give 3 fractions—a faster moving fraction containing the equatorial isomer, a slower moving fraction containing the axial isomer, and a fraction containing a mixture of both isomers. Each fraction was concentrated to a small volume, acidified with 1N H$_2$SO$_4$, sand subjected to a short column of C18 silica gel. The column was washed with water and eluted with 80% acetonitrile. The eluate was concentrated to a small volume and lyophilized. The 3 fractions afforded 4'-deamino-4'-hydroxy pradimicin FA-2 axial isomer (XXVI, 3 mg, 3%), the equatorial isomer (XXVII, 5.4 mg, 4%), and a mixture thereof.

4'-Deamino-4'-hydroxy pradimicin FA-2 (axial isomer, XXVI)
MP:>220° C. (grad. dec.).
UV $\lambda_{max}$ (0.01N NaOH) nm ($E_1{}_{cm}^{1\%}$): 320 (134), 497 (129).
IR $\nu_{max}$ (KBr) cm$^{-1}$: 3272, 2917, 1739, 1607.
$^1$H NMR (DMSO-d$_6$) δ:1.10 (3H, d, J=6.4 Hz, 5'-CH$_3$), 2.34 (3H, s, 3-CH$_3$), 3.69 (1H, dd, J=5.5 & 11.1 Hz, 5"-eq-H), 3.95 (3H, s, 11-OCH$_3$), 4.40 (1H, d, J=6.8 Hz, 1"-H), 4.63 (1H, d, J=7.7 Hz, 1'-H), 6.90 (1H, s, 10-H), 7.10 (1H, s, 4-H), 7.27 (1H, s, 12-H), 7.99 (1H, s, 7-H).
HPLC*: Retention time 9.8 minutes.
The equatorial isomer (XXVII)
MP:>220° C. (grad.dec.)
UV $\lambda_{max}$ (0.01N NaOH) nm ($E_1{}_{cm}^{1\%}$): 318 (151), 497 (140).
IR $\nu_{max}$ (KBr) cm$^{-1}$: 3408, 1733, 1607.
$^1$H NMR (DMSO-d$_6$) δ:1.15 (3H, d, J=6.0 Hz, 5'-CH$_3$), 2.32 (3H, s, 3-CH$_3$), 3.75 (1H, dd, J=5.1 & 11.1 Hz, 5"-eq-H), 3.94 (3H, s, 11-OCH$_3$), 4.45 (1H, d, J=7.3 Hz, 1"-H), 6.87 (1H, s, 10-H), 7.02 (1H, s, 4-H), 7.24 (1H, s, 12-H), 7.93 (1H, s, 7-H).
HPLC*: Retention time 8.5 minutes.
*HPLC conditions same as described in Example 2.

Example 4. Preparation of benanomicin A (a) The procedure of Example 2, step (a), was followed using pradimicin C HCl (150 mg, 0.16 mmol) and 3.5-di-t-butyl-1,2-benzoquinone (110 mg, 0.5 mmol) to provide the corresponding imine (XXVIII, 212 mg).
IR $\nu_{max}$ (KBr) cm$^{-1}$: 1622, 1607, 1259, 1080.
UV $\lambda_{max}$ (MeOH) nm ($E_1{}_{cm}^{1\%}$): 288 (259), 478 (98).
$^1$H NMR (DMSO-d$_6$) δ:0.96 (3H, d, J=7 Hz, 5'-CH$_3$), 1.22 (9H, s t-Bu), 1.25 (9H, s, t-Bu), 1.29 (3H, d, J=7 Hz, alanyl-CH$_3$), 2.22 (3H, s, 3-CH$_3$), 3.90 (3H, s, OCH$_3$), 4.82 (1H, d, J=8 Hz, 1'-H), 4.94 (1H, br)*, 5.09 (1H, br)*, 5.70 (1H, br)*, 5.80 (1H, br)*, 5.98 (1H, s)*, 6.19 (1H, s)*, 6.42 (1H, d, J=2 Hz, phenyl-H), 6.49 (1H, d, J=2 Hz, phenyl-H), 6.71 (1H, d, J=2 Hz, 10-H), 6.91 (1H, s, 4-H), 7.13 (1H, d, J=2 Hz, 12-H), 7.47 (1H, br)*, 7.68 (1H, s, 7-H), 13.22 (1H, s)*, 14.80 (1H, s)*.
*Disappeared by the addition of D$_1$O.

(b) The procedure of Example 2, step (b), was followed using the imine obtained from step (a) above (210 mg, 0.20 mmol) to provide the corresponding ketone (XXIX, 147 mg 89%).
IR $\nu_{max}$ (KBr) cm$^{-1}$: 1738 (weak), 1607.
UV $\lambda_{max}$ (0.02N NaOH) nm ($E_1{}_{cm}^{1\%}$): 318 (171), 498 (143).
$^1$H NMR (DMSO-d$_6$) δ:3.96 (3H, s, 11-OCH$_3$), 6.9 (1H, s, 4-H), 7.32 (1H, s, 12-H).

(c) The procedure of Example 2, step (c), was followed using the ketone obtained above (80 mg, 0.097 mmol) to provide benanomicin A (II, 8.5 mg, 11%), its 4'-equatorial isomer (XXX, 5 mg, 6%) and mixture thereof (5 mg).
Benanomicin A (II)
MP:>220° C. (grad. dec.).
UV $\lambda_{max}$ (NaOH—MeOH) nm ($E_1{}_{cm}^{1\%}$): 277 (233), 318 (92), 499 (108).
IR $\nu_{max}$ (KBr) cm$^{-1}$: 3402, 1733, 1623, 1607.
$^1$H NMR (DMSO-d$_6$) δ:1.12 (3H, d, J=6.4 Hz, 5'-CH$_3$), 1.33 (3H, d, J=7.3 Hz, 17-CH$_3$), 2.27 (3H, s, 3-CH$_3$), 3.90 (3H, s, 11-OCH$_3$), 4.63 (1H, d, J=7.7 Hz, 1'-H), 6.71 (1H, d, J=2.1 Hz, 10-H), 6.94 (1H, s, 4-H), 7.11 (1H, d, J=2.1 Hz, 12-H), 7.74 (1H, s, 7-H).

MS (FAB): (Positive) 828 (M+H)$^+$, 850 (M+Na)$^+$ (Negative) 827 (M)$^-$

HPLC*: Retention time 9.5 minutes.

The equatorial isomer (XXX)

MP:>250° C. (grad.dec.).

UV $\lambda_{max}$ (NaOH—MeOH) nm ($E_1{}_{cm}{}^{1\%}$) 277 (209), 318 (88), 502 (103).

IR $\nu_{max}$ (KBr) cm$^{-1}$: 3398, 1733, 1627, 1607.

$^1$H NMR (DMSO-d$_6$) δ:1.15 (3H, d, J=6.0 Hz, 5'-CH$_3$), 1.33 (3H, d, J=7.3 Hz, 17-CH$_3$), 2.29 (3H, s, 3-CH$_3$), 3.75 (1H, dd, J=5.6 & 11.1 Hz, 5"-eq-H), 3.93 (3H, s, 11-OCH$_3$), 4.45 (1H, d, J=7.3 Hz, 1"-H), 6.79 (1H, s, 10-H), 6.95 (1H, s, 4-H), 7.18 (1H, s, 12-H), 7.84 (1H, s, 7-H).

MS (FAB): (Positive) 828 (M+H)$^+$, 850 (M+Na)$^+$ (Negative) 826 (M-H)$^-$

HPLC*: Retention time 8.8 minutes.

*HPLC: column, Senshu Pak SSC-ODS-262; solvent, CH$_3$CN:pH 7 buffer=15:85; flow rate, 2 ml/minute.

Compounds Prepared in Examples 1–4

Example 1

Step (a)

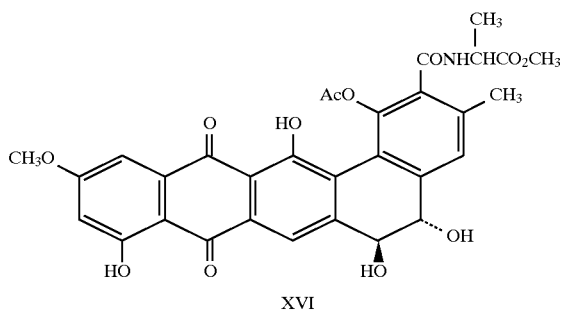

XVI

Step (c)

Fraction 1

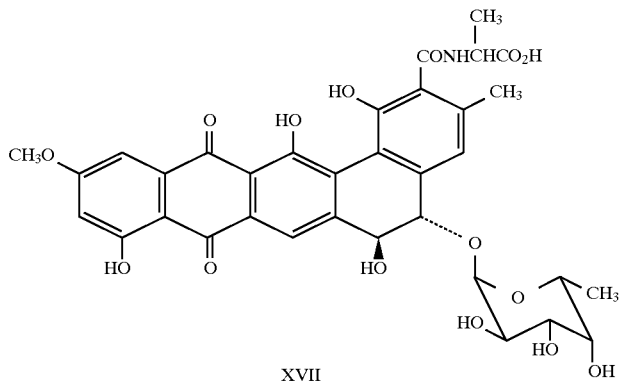

XVII

Fraction 2

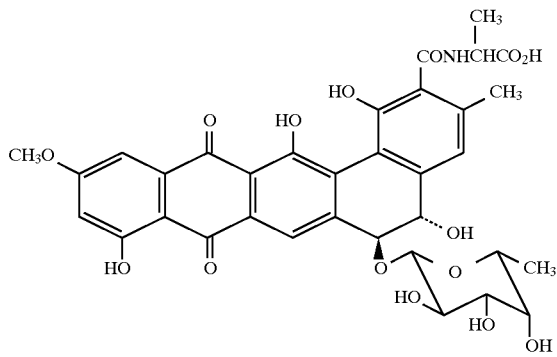

XVIII

Fraction 3
-continued
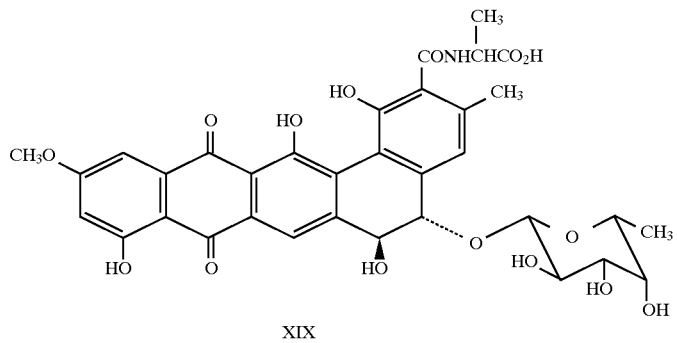
XIX
Examples 2–4
Step (a)
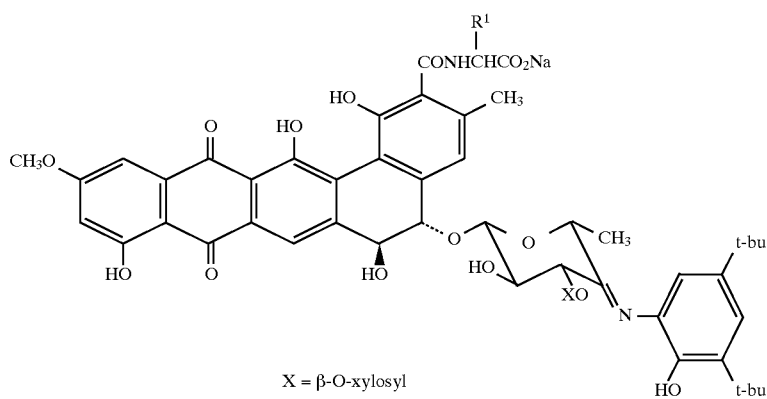
X = β-O-xylosyl
Ex. 2 -- XX: $R^1$ = H
Ex. 3 -- XXIV: $R^1$ = $CH_2OH$
Ex. 4 -- XXVIII: $R^1$ = $CH_3$
Step (b)
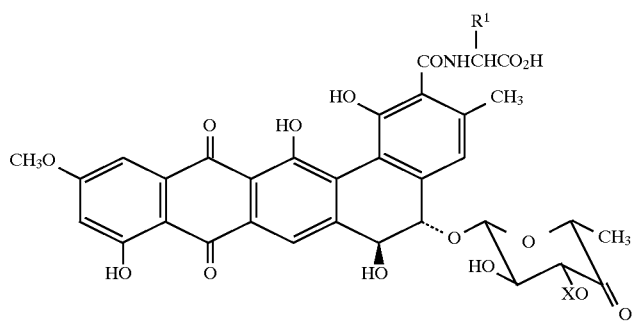
X = β-O-xylosyl
Ex. 2 -- XXI: $R^1$ = H
Ex. 3 -- XXV: $R^1$ = $CH_2OH$
Ex. 4 -- XXIX: $R^1$ = $CH_3$ Step (c)

axial isomer

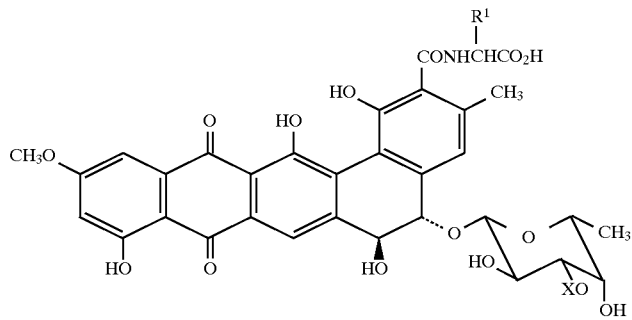

X = β-O-xylosyl
Ex. 2 -- XXII:  R¹ = H
Ex. 3 -- XXVI:  R¹ = CH₂OH
Ex. 4 -- II equatorial isomer

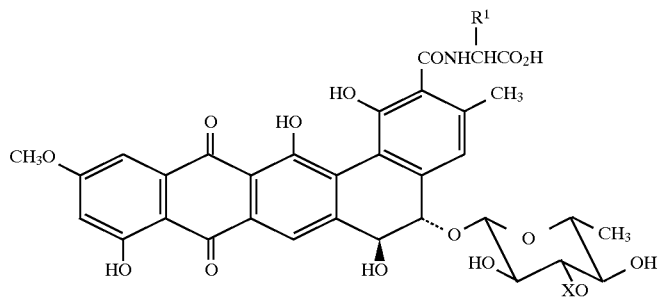

X = β-O-xylosyl
Ex. 2 -- XXIII:  R¹ = H
Ex. 3 -- XXVII:  R¹ = CH₂OH
Ex. 4 -- XXX:   R¹ = CH₃

What is claimed is:

1. A compound having the formula

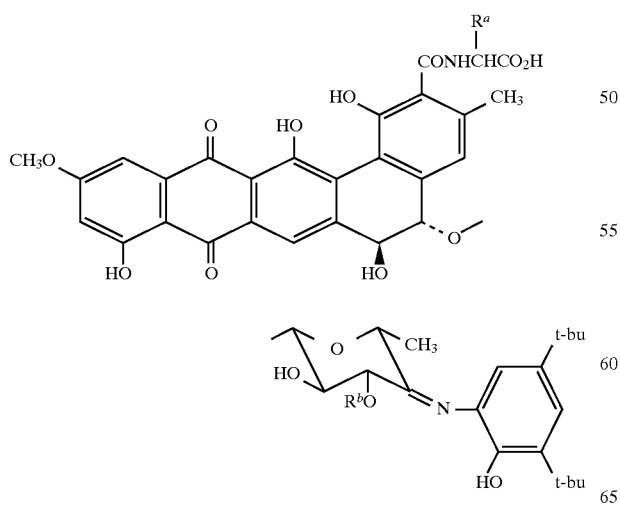

wherein $R^a$ is H, methyl, or hydroxymethyl, and when $R^a$ is methyl or hydroxymethyl, the resulting amino acid has the D-configuration; $R^b$ is H or β-D-xylosyl; or a salt thereof; or an ester thereof.

2. A compound having the formula

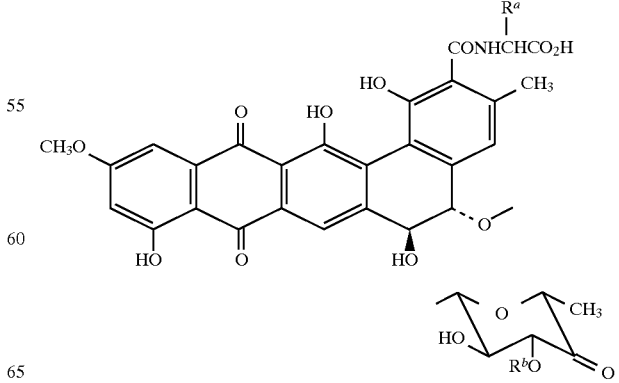

wherein $R^a$ and $R^b$ are as defined in claim 1; or a salt thereof; or an ester thereof.

3. A process for preparing a compound of the formula

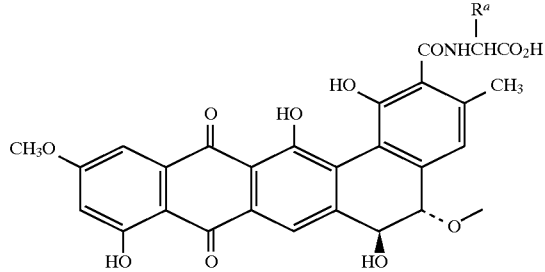

wherein $R^a$ and $R^b$ are as defined in claim 1, or a pharmaceutically acceptable salt thereof, which comprises the steps of:

(a) reacting a compound having the formula

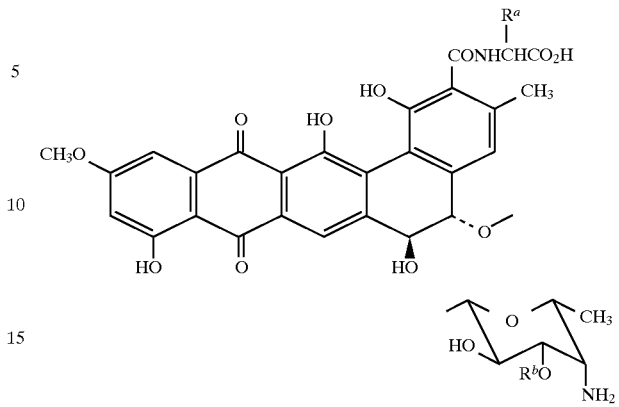

wherein $R^a$ and $R^b$ are as defined above, or a salt thereof, with 3,5-di-t-butyl-1,2-benzoquinone in an inert organic solvent to form the corresponding imine;

(b) converting the product of (a) into the corresponding ketone in the presence of an acid catalyst;

(c) reducing the product of (b) to the corresponding alcohol; and (d) separating the isomers.

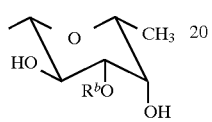

* * * * *